United States Patent
Müller-Späth et al.

(10) Patent No.: US 11,180,526 B2
(45) Date of Patent: Nov. 23, 2021

(54) PURIFICATION METHOD AND USES THEREOF

(71) Applicant: ChromaCon AG, Zurich (CH)

(72) Inventors: Thomas Müller-Späth, Zürich (CH); Lars Aumann, Zürich (CH); Michael Bavand, Lenzburg (CH)

(73) Assignee: ChromaCon AG, Zurich (CH)

( * ) Notice: Subject to any disclaimer, the term of this patent is extended or adjusted under 35 U.S.C. 154(b) by 0 days.

(21) Appl. No.: 16/071,277

(22) PCT Filed: Jul. 10, 2017

(86) PCT No.: PCT/EP2017/067190
§ 371 (c)(1),
(2) Date: Jul. 19, 2018

(87) PCT Pub. No.: WO2018/011102
PCT Pub. Date: Jan. 18, 2018

(65) Prior Publication Data
US 2020/0031863 A1 Jan. 30, 2020

(30) Foreign Application Priority Data
Jul. 13, 2016 (EP) .................................. 16179273

(51) Int. Cl.
*C07K 1/16* (2006.01)
*B01D 15/18* (2006.01)
(Continued)

(52) U.S. Cl.
CPC ............ *C07K 1/16* (2013.01); *B01D 15/1807* (2013.01); *B01D 15/1871* (2013.01);
(Continued)

(58) Field of Classification Search
CPC ........ G01N 30/02; G01N 30/26; G01N 30/34; G01N 30/38; G01N 30/44; G01N 30/46;
(Continued)

(56) References Cited

U.S. PATENT DOCUMENTS 3,220,164 A    11/1965   Golay
5,443,623 A *   8/1995   Jonas ................... B01D 53/047
                                                             95/101
(Continued)

FOREIGN PATENT DOCUMENTS

EP          2 772 289 A1      9/2014
WO      WO-9948587 A1 *    9/1999           B01D 15/1871
(Continued)

OTHER PUBLICATIONS

International Search Report for PCT/EP2017/067190 dated Sep. 15, 2017 [PCT/ISA/210].

*Primary Examiner* — Katherine Zalasky McDonald
(74) *Attorney, Agent, or Firm* — Sughrue Mion, PLLC

(57) ABSTRACT

A cyclic chromatographic purification method for the isolation of a product from a feed mixture consisting of the product and at least one further component representing impurities, which impurities bind stronger to the chromatographic stationary phase than the product is given. The method uses at least two chromatographic adsorbers as chromatographic stationary phase, grouped into only one first adsorber section (1) and one second adsorber section (2), wherein if an adsorber section comprises more than one chromatographic adsorber these are permanently connected in series, wherein the first adsorber section (1) has a first adsorber section inlet and a first adsorber section outlet, and the second adsorber section (1) has a second adsorber section inlet and a second adsorber section outlet.

23 Claims, 4 Drawing Sheets

(51) Int. Cl.
  *B01D 15/30*   (2006.01)
  *B01D 15/36*   (2006.01)
  *B01D 15/38*   (2006.01)
  *B01D 15/34*   (2006.01)
  *B01D 15/42*   (2006.01)

(52) U.S. Cl.
  CPC ......... *B01D 15/305* (2013.01); *B01D 15/361* (2013.01); *B01D 15/3847* (2013.01); *B01D 15/34* (2013.01); *B01D 15/428* (2013.01)

(58) Field of Classification Search
  CPC .. G01N 30/461; G01N 30/462; G01N 30/463; G01N 30/368; B01D 15/08; B01D 15/18; B01D 15/1814; B01D 15/1828; B01D 15/1864; B01D 15/1871; B01D 15/1878; B01D 15/20; B01D 15/203; B01D 15/3804; B01D 15/428
  See application file for complete search history.

(56) References Cited

U.S. PATENT DOCUMENTS

| | | | |
|---|---|---|---|
| 8,440,086 B2* | 5/2013 | Muller-Spath | B01D 15/1821 210/659 |
| 9,018,137 B2* | 4/2015 | Muller-Spath | B01D 15/1807 506/12 |
| 9,073,970 B2* | 7/2015 | Muller-Spath | B01D 15/1864 |
| 10,099,156 B2* | 10/2018 | Muller-Spath | B01D 15/1864 |
| 10,948,483 B2* | 3/2021 | Muller-Spath | G01N 33/52 |
| 2013/0046080 A1 | 2/2013 | Jeon et al. | |
| 2016/0074775 A1* | 3/2016 | Cvetkovic | B01D 15/125 210/650 |

FOREIGN PATENT DOCUMENTS

| | | |
|---|---|---|
| WO | 2013/083482 A1 | 6/2013 |
| WO | 2014/166799 A1 | 10/2014 |

* cited by examiner

PURIFICATION METHOD AND USES THEREOF

CROSS REFERENCE TO RELATED APPLICATIONS

This application is a National Stage of International Application No. PCT/EP2017/067190, filed on Jul. 10, 2017, which claims priority from European Patent Application No. 16179273.4, filed on Jul. 13, 2016.

TECHNICAL FIELD

The present invention relates to a cyclic chromatographic purification method, in particular for polishing chromatography for use in the purification of therapeutic proteins including antibodies.

PRIOR ART

A chromatographic process for the purification of active substances such as therapeutic proteins and peptides typically includes a number of individual chromatographic steps. The product of interest is typically accompanied by a number of impurities that have to be removed. In chromatography, the different interactions of the product of interest and the impurities with the stationary phase, i.e. the adsorbent material, are exploited. The stationary phase is contained in a vessel suited for chromatographic operation (typically a column or a membrane adsorber) and this combination is referred to as "adsorber" in the following.

The interactions of the product of interest and the impurities with the stationary phase are strongly dependent on their molecular properties such as charge and size, which in turn are influenced by properties of the liquid that is pumped through the adsorber and in which product and impurities are dissolved. By modifying the properties of the liquid that is flowing through the adsorber (the so-called mobile phase), the binding properties of the product or the impurities can be changed in a way that separation is achieved. Under certain conditions binding (adsorption) of the product to the stationary phase may be promoted while under other conditions instead the non-binding (desorption) of the product may be promoted. The same applies for the impurities. Typical modifications of the mobile phase encompass changes of the ionic strength, pH value or organic solvent content or composition.

In so called bind/elute chromatography (e.g. in affinity chromatography) the mobile phase conditions are chosen such that the product of interest is bound to the stationary phase, while the impurities are flowing through. After the stationary phase has been loaded with a certain amount of product, the adsorbent is typically washed with a mobile phase that removes residual impurities from the adsorbent, leaving the product adsorbed on the stationary phase. To recover the product, the mobile phase conditions are then changed such that the interactions between the product of interest and the stationary phase are disrupted and the product is released and is washed out of the adsorbent for collection. The first step of a chromatographic purification sequence is frequently a bind/elute process due to its ability of concentrating the product contained in a dilute feedstock and removing impurities. The bind/elute process is discontinuous in a sense that the product concentration in the stream that exits the adsorber is not constant over time. In certain applications in which the product is synthesized in a continuous reactor it is desirable to also run the chromatographic purification sequence in a continuous mode to minimize intermediate hold/storage steps.

In flow-through chromatography, the stationary phase and the conditions of the mobile phase are chosen such that the impurities are adsorbed more strongly on the stationary phase than the product of interest, which allows the product to pass through the adsorber ahead of the impurities. In flow-through chromatography, a continuous operation is possible with constant feed and product flow rates, however a significant product concentration increase cannot be achieved because feed and product stream are of the same magnitude. A generic flow-through process includes an equilibration step, a loading step and a regeneration step. The product is recovered during the loading step. In the regeneration step, the adsorber is cleaned and re-equilibrated in order to clear bound impurities and to prepare the adsorber for the next run. If the loading step is longer than the regeneration step, two flow-through adsorbers working side-by-side can ensure a continuous feed and outlet flow, interrupted only by switching inlets and outlets of the adsorbers ("flip-flop" operation).

When developing flow-through processes, the chromatographer tries to modify the conditions of the load material (e.g. ionic strength and pH) such that the product of interest is not-adsorbing and passing through the adsorber while the impurities are strongly adsorbing and completely retained. However, in cases where the impurities and the product of interest have very similar adsorptive properties, reaching this objective may be impossible and instead, only conditions can be found in which the impurities are adsorbing slightly more strongly on the stationary phase than the product so that an acceptable product purity is reached. It is obvious that under the conditions of similar adsorptive properties the product that leaves the adsorber for collection is followed by the impurities soon as the loading of the adsorber progresses, leading to a low effective capacity for the product. In other words the adsorptive properties (usually quantified by the so called retention factors) and the capacity correlate and if the former ones a similar for product and impurities, the latter tend to be similar too. A lower capacity of the adsorber for the impurities means that loading has to be stopped much sooner after starting the load and the adsorber has to be cleaned and regenerated for the next run than under conditions with high capacity for the impurities.

This means that the productivity, which is defined as the amount of product purified using the process per time and per adsorber volume, is reduced because less product is produced per cycle. Thus the lower capacity leads to a lower productivity.

A process where the loading conditions are chosen such that some of the stronger adsorbing compounds are fully retained while the other less strongly adsorbing impurities are not retained at all will deliver low purity product, because the less strongly adsorbing impurities are flowing through together with the product. High loading volumes leading to high productivities (i.e. a larger amounts of product produced per time and adsorber volume) can be achieved when operating in this way because only a fraction of the impurities is retained but the product may not fulfil specifications. This shows that in state of the art flow-through processes there is a trade-off between productivity and product purity.

The trade-off is more pronounced in the case where the ratio of impurities and product is high, for instance like in the case of aggregates in monoclonal antibody (mAb) cell culture harvest, where levels of 0.5-15% aggregates have been reported. The trade-off is less pronounced in the case of trace contaminant removal such as Host Cell Proteins, DNA, and viruses that are typically present in the feed material in ppm amounts (parts per million). Summarizing, the aims of obtaining a high purity and a high productivity are mutually exclusive in flow-through chromatography when the product and the impurities have similar adsorptive properties, such as in many cases of product related impurity removal.

SUMMARY OF THE INVENTION

The present invention aims at alleviating the trade-off of productivity and product purity of state of the art processes to obtain a flow-through process with high productivity and product purity.

All flow-through processes need to address the challenge of how to recover the product that remains in the adsorber at the end of the loading stage. This product can be only recovered through washing with mobile phase that is adjusted such that the product is washed out and the impurities remain in the adsorbers. In practice this can be very difficult to achieve and in order not to violate the purity specification a fraction of the product may unavoidably be left behind. This product is then cleared in the subsequent cleaning step and lost, lowering the yield of the process.

Another variation of flow-through chromatography working under high capacities makes use of displacement effects: The capacity of the adsorber for both product and impurities can be strongly increased by choosing appropriate mobile phase properties. When the adsorber is loaded both product and impurities are strongly retained on the adsorber and during the loading initially no product elutes from the adsorber as the product accumulates in the adsorber. As the loading progresses the impurities that adsorb on the stationary phase even stronger than the product displace the product from the stationary phase, eventually pushing it off of the adsorber.

Generally flow-through methods can reach higher loading rates than bind/elute steps, especially in cases of low impurity concentration in the feed which leads to a very slow saturation of adsorber with impurities and ensures long loading times. Loads of 10.000-20.000 g of mAb per liter of adsorber have been reported for flow-through operations while in bind/elute chromatography maximum loads of around 200 g of mAb per liter of adsorber can be achieved which is 100-fold less. One drawback of flow-through chromatography is that it is not possible to separate compounds from the product of interest that are adsorbing weaker.

Moreover the impurities may comprise multiple compounds themselves, some of them exhibiting similar adsorptive properties as the product and some having very different adsorptive properties. As described earlier, in order to obtain high product purity, it is necessary to adjust the loading conditions such that the product is adsorbing weaker than most impurities.

The proposed process is fundamentally different from periodic countercurrent processes with two or more adsorbers (such as e.g. the one disclosed in WO2014166799) for the following reasons:

1. In the invented process the compound of interest, i.e. the product, is flowing through the adsorbers while it is retained on the adsorbers in the prior art process. This holds true in both the batch phase and the interconnected phase.

2. In the "Batch" phase of the presented process, product recovery and regeneration steps are decoupled and performed on separate adsorbers. In the process according to WO2014166799 and other processes these tasks are performed on the same adsorber in the "Batch" phase B.

3. In the invented process an inline dilution step is utilized in the interconnected state of the adsorbers that ensures that the compounds breaking through from the first adsorber section are re-adsorbed on the second adsorber section and do not contaminate the product compound that is flowing through. The inline dilution step can be replaced by supplementing the stream exiting the first adsorber section outlet with feed mixture, having a similar or same effect. This step is completely absent in WO2014166799 where it would be useless because the compound of interest is retained rather than flowing through the adsorbers as in the invented process.

4. Moreover, as indicated above, the proposed process relies on the use of non-affinity chromatography which is due to the fact that usually in the feed stream there are multiple impurities and only one target compound. Affinity materials are very selective towards specific individual compounds, binding these compounds very strongly while not binding the others. A process as described in WO2014166799 run with the intention to isolate the compound of interest in the flow-through with an affinity adsorbent material directed at one individual target compound would not provide a satisfactory impurity clearance as the desorbing conditions that are required for product elution would correspond to desorbing conditions for the majority of the impurities which would pass through the adsorber together with the product unbound. Thus, the process according to WO2014166799 wherein "product" and "waste" are simply exchanged would not be functional.

5. A process as described in WO2014166799 run with the intention to isolate the product of interest in flow-through mode relying on displacement effects with strongly adsorbing product and impurities would lead to the problem of separation of the product and the impurities during the batch phase (B) where the adsorber needs to be regenerated. Elution of the remaining product as foreseen in WO2014166799 would lead to very low purity of this product because the eluted adsorber contains a very high amount of impurities. On the other hand, not recovering this product would lead to yield losses.

The present invention relates to countercurrent chromatography processes operated in flow-through mode.

It was surprisingly found that continuous flow-through chromatography can be realized in a multi-adsorber setup by an innovative combination of advantages of flow-through chromatography, sequential loading chromatography, inline dilution, and by, if needed, applying a process control strategy based on comparison of detector signals at the outlet of each individual adsorber section. The novel process including control methods allows running flow-through chromatography with excellent productivity, capacity utilization and, most importantly purity advantages without sacrificing product yield.

The process comprises a sequence of steps wherein the adsorbers are organized in sections with each adsorber section containing at least one adsorber and the sections are either operated as individual sections with independent inlets and outlets or the adsorber sections are operated in interconnected mode wherein the outlet of one adsorber section is directed to the inlet of the other adsorber section. The individual adsorbers within each section are permanently connected in series. Both adsorber sections contain the same number of individual adsorbers and all adsorbers in the process contain the same stationary phase. In specifically defined interconnected steps the stream exiting one adsorber section is diluted in-line with another stream before entering the next adsorber section. This offers the option to modify the properties of the stream exiting the first adsorber section in order to change the adsorptive properties of the product and the impurities for the next adsorber section.

The process is operated cyclically, i.e. after having completed one sequence of steps, a new identical sequence is started containing the same steps. Typically the process is repeated at least once, preferably at least 5 or 10 times.

More specifically, the present invention relates to a cyclic chromatographic purification method for the isolation of a product from a feed mixture consisting of the product and at least one further component representing impurities, with the properties of the feed being such that the impurities bind stronger to the chromatographic stationary phase than the product.

The proposed method is using at least two chromatographic adsorbers as chromatographic stationary phase, grouped into only one first adsorber section and one second adsorber section. If an adsorber section comprises more than one chromatographic adsorber these are permanently connected in series.

The first adsorber section has a first adsorber section inlet and a first adsorber section outlet, and the second adsorber section has a second adsorber section inlet and a second adsorber section outlet.

The proposed method comprises, preferably consists of the following steps in order:

a. a first interconnected step IC1a, wherein the first adsorber section outlet is connected to the second adsorber section inlet during an first interconnected timespan $t_{IC_a}$, wherein the first adsorber section is loaded via the first adsorber section inlet with feed mixture and wherein product is collected from the second adsorber section outlet;

b. a second interconnected step IC1b, wherein the first adsorber section outlet is connected to the second adsorber section inlet during a second interconnected timespan $t_{IC_b}$, wherein the first adsorber section is loaded via the first adsorber section inlet with a first washing buffer to transfer product unbound in the first absorber section into the second adsorber section and wherein the stream exiting the first adsorber section outlet is
either diluted inline before entering the second adsorber section inlet (embodiments A and B)
or is supplemented with feed mixture (embodiment C)
and wherein product is collected from the second adsorber section outlet, normally during the whole second interconnected timespan La);

c. a first batch step B1, wherein during a batch timespan tB said first and second adsorber sections are disconnected and
wherein the first adsorber section is cleaned and regenerated to remove impurities
and the first adsorber section outlet is directed to waste
and wherein the second adsorber section inlet is
either loaded with second washing buffer (embodiment A)
or loaded with feed mixture (embodiments B and C)
and product is collected from the second adsorber section outlet;

d. a third interconnected step IC2a, wherein the first adsorber section performs tasks of the second adsorber section in the first interconnected step, and the second adsorber section performs tasks of the first adsorber section in the first interconnected step;

e. a fourth interconnected step IC2b, wherein the first adsorber section performs tasks of the second adsorber section in the second interconnected step, and the second adsorber section performs tasks of the first adsorber section in the second interconnected step;

f. a second batch step B2, wherein the first adsorber section performs tasks of the second adsorber section in the first batch step, and the second adsorber section performs tasks of the first adsorber section in the first batch step.

First, second and further washing buffers as mentioned can be the same, and individually looked at can be more than one type of washing buffer, so which can be the same or different, and which are then used sequentially. So for example the first and second washing buffer as mentioned above can be the same buffer having the same composition. It is however also possible that the first and second washing buffer are different from each other, so they have a different composition.

Also it is for example possible that the use of the first washing buffer in step b. (or of the second washing buffer in step c., respectively) entails using two or even several different types of this first washing buffer (for example having different compositions/concentrations) which are used consecutively in this step.

The same holds true for the in-line dilution buffer, mentioned below, also here the in-line dilution buffer can be one single system or it may be formed by two or even several different types of buffers which are used sequentially depending on the needs and requirements. In particular in case the interconnected washing conditions can be chosen such that the impurities remain strongly bound in the upstream adsorber (see p2. L25ff) while the product is completely transferred to the downstream adsorber, the in-line dilution buffer can be replaced by feed, which allows an operation of the process with an uninterrupted feed flow (embodiment C). This can be desirable depending on the manufacturing context.

In phase IC1a, the first and the second adsorber sections are interconnected and the first adsorber section is loaded with feed mixture. The product is collected from the outlet of the second adsorber section while the impurities are retained. Thereby the first adsorber section is loaded beyond impurity breakthrough such that the capacity of the upstream adsorber section is exploited to a great extent. Any impurities breaking through from the upstream adsorber section are retained in the second adsorber section, staying out of the product that is collected at the outlet of the second adsorber section.

Thereafter, in phase IC1b, the first and the second adsorber sections remain interconnected. The first adsorber is loaded with a washing buffer to flush all the product out of the first adsorber section. During this step, frequently buffer conditions are not ideal resulting in a fraction of the impurities being washed out of the first adsorber section together with the product. In order to prevent these impurities from ending up in the product pool, the stream exiting the first adsorber is diluted in line before entering the second adsorber. This ensures binding of the impurities on the second adsorber. In embodiments A and B, buffer is used for inline dilution, while in embodiment C, feed is used.

Thereafter in phase B1, the formerly upstream adsorber is regenerated, i.e. it is cleaned to remove the impurities and re-equilibrated for the uptake of new feed. At the same time, the formerly downstream column is continued to be washed with buffer (embodiment A) or loaded with feed mixture (embodiment B and C) in anticipation of phase IC2a.

In phases IC2a, IC2b, and B2, the same tasks as in IC1a, IC1b and B1 are carried out, respectively, just with the adsorber sections in opposite order. The sequence of phases IC1a, IC1b and B1, IC2a, IC2b, and B2 represents one cycle. After one cycle has been completed, a new cycle can be started. In so called cyclic steady state, product and impurity profiles and concentrations are matching from cycle to cycle and product of uniform quality is produced.

Embodiment A refers to the proposed process wherein in phases B1 and B2 a washing step is run on the formerly downstream adsorber section in order to push out remaining product of that adsorber section and to equilibrate the adsorber section (in FIG. 1: section 2 in phase B1 and section 1 in phase B2). In this embodiment, washing buffer is used for inline dilution in phases IC1b and IC2b.

Embodiment B refers to the proposed process wherein in phases B1 and B2 a feeding step is run in the formerly downstream adsorber section. In this embodiment, buffer is used for inline dilution in phases IC1b and IC2b.

Embodiment C refers to the presented process wherein in phases B1 and B2 a feeding step is run in the formerly downstream adsorber section. In this embodiment, feed is used for inline dilution in phases IC1b and IC2b. This embodiment potentially enables running with a uniform feed flow rate in all process steps, so it allows a fully continuous separation process.

The selection of the embodiments is dependent on the objective of the purification process and the input parameters, mainly on the product concentration in the feed mixture as illustrated in the examples.

Embodiment A is likely to be selected when operating the process in the context of a manufacturing environment where the previous and subsequent purification steps are operated in batch mode, i.e. in a cyclic, discontinuous manner. Moreover it would be run in the case of very difficult separation between product and impurities and when high feed titer is used.

Embodiment B is likely to be selected when operating the process in the context of a manufacturing environment where the previous and subsequent purification steps are operated in batch mode, i.e. in a cyclic, discontinuous manner. Moreover it would be run in the case where the separation of product and impurities is comparably simpler and when the feed titer is high. The throughput of this embodiment is slightly higher than the one of embodiment A.

Embodiment C is likely to be selected when operating the process in a fully continuous processing environment wherein the feed is delivered with a constant flow rate. According to a preferred embodiment, each adsorber section consists of only one adsorber such that the total number of adsorbers in the process is two.

In order to reach cyclic steady state faster, the cyclic phase of the process can be preceded by a startup step that accounts for the adsorbers being devoid of feed material initially. Before for the first time carrying out the first interconnected step thus preferably a start-up step BSU is carried out, in which during a batch timespan $t_{BSU}$ said adsorber sections are disconnected and an equilibrated adsorber section to be taking the place of the first adsorber section in the subsequent first interconnected step is loaded with feed mixture via the first adsorber section inlet and product is collected from first adsorber section outlet, while the second adsorber section is either being equilibrated or already equilibrated and inactive.

The cyclic phase of the process can be concluded by a shutdown sequence that ensures that the product remaining on the adsorbers is recovered while no new material is loaded and the adsorbers are cleaned and re-equilibrated.

After termination of the desired cycles of steps a.-f. the procedure can thus followed by a shut-down sequence BSD, wherein during a first batch timespan $t_{BSDa}$ said adsorber sections are disconnected and the adsorber section having been subjected to washing in the preceding second batch step B2 is washed such that product is collected from the adsorber section outlet; and wherein during a second timespan $t_{BSDb}$ both adsorber sections are regenerated;

Summarizing, the presented process comprises configurations where the adsorber sections are connected in series and sections where the adsorber sections are operated independently.

Thus, the process can be regarded as a hybrid process between a process using a single adsorber section and a process that uses two adsorber sections connected in series.

In comparison with a conventional process that uses a single adsorber section, the presented process has the following advantage:

The upstream adsorber section can be loaded beyond the capacity of the impurities without compromising product purity of the product collected at the outlet of the downstream adsorber section. This allows a much higher loading of the upstream adsorber section in comparison to the load of the single adsorber section and increases throughput.

A potential breakthrough of impurities during the washing step and contamination of the product pool can be avoided by means of inline dilution in between the first and the second adsorber section.

In comparison with a conventional process that uses two adsorber sections connected in series permanently, the presented process has the following advantage:

A potential breakthrough of impurities during the washing step from the downstream adsorber section and contamination of the product pool can be avoided by means of inline dilution in between the first and the second adsorber section, which is a feature of the presented process but absent in a conventional process that would use two adsorber sections connected in series.

The adsorber sections can be disconnected and the formerly upstream adsorber section can be cleaned independently of the formerly downstream section. This ensures that only the upstream adsorber section, whose capacity for impurities is exploited to a great extent, is cleaned. By cleaning only the upstream adsorber section, the cleaning can be completed in half the time in comparison to cleaning of two adsorber sections in series, which significantly increase throughput.

The described chromatographic method is very flexible with respect to the utilized stationary phase. Applicable adsorbers can be columns filled with adsorbent particles, fibers, monoliths or membranes. The process is compatible with single-use and multi-use devices. The chromatographic stationary phase in the adsorbers can thus be in the form of particles, such as beads, or of membranes or monoliths or fibers and wherein the adsorbers are single-use or multi-use devices, and wherein preferably the chromatographic stationary phase in the adsorbers is a non-affinity material with a propensity to withhold the product and the impurities depending on their chemical nature in a gradual manner.

The chromatographic adsorption can be based on hydrophobic interaction, multi-modal interaction or ion exchange.

A detector can be located at the outlet of each adsorber section wherein the changes in the detected signal over time during the first and second interconnected phases IC1a, IC1$b$, IC2$a$, IC2$b$ are used to determine the first and second interconnected timespans (tICa, tICb), respectively.

The detector can be selected from the group consisting of an UV detector, a visible light detector, an IR detector, a fluorescence detector, a light scattering detector, a refractive index detector, a pH detector, a conductivity detector, an at-line HPLC detector, and a mass spectrometry detector.

The product can be one or a group of chemical reaction products, chemical separation products, biochemical reaction products, biological products, wherein preferably the reaction products are natural products, metals, antibodies, antibody fragments, fusion proteins, recombinant glycoproteins, and/or plasma proteins, or derivatives and/or combinations and/or mixtures thereof.

The product can be an antibody monomer and the impurities include at least one antibody dimer and/or multimer.

In the second interconnected step IC1$b$, IC2$b$, the stream exiting the first adsorber section outlet can be diluted inline, e.g. with buffer, before entering the second adsorber section inlet, wherein in the first batch step the second adsorber section inlet can be loaded with a second washing buffer, and wherein in the second batch step the first adsorber section inlet can be loaded with said washing buffer, which represents the above-mentioned embodiment A.

In the second interconnected step IC1$b$, IC2$b$, the stream exiting the first adsorber section outlet can be diluted inline, e.g. with buffer, before entering the second adsorber section inlet, wherein in the first batch step the second adsorber section inlet can be loaded with feed mixture, and wherein in the second batch step the first adsorber section inlet can be loaded with feed mixture, which represents the above-mentioned embodiment B.

In the second interconnected step the stream exiting the first adsorber section outlet can be supplemented with feed mixture, and wherein in the first batch step the second adsorber section inlet is loaded with feed mixture, which represents the above-mentioned embodiment C.

In the second interconnected step IC1$b$, IC2$b$, the stream exiting the first adsorber section outlet can be diluted inline before entering the second adsorber section inlet with an inline dilution buffer.

Furthermore the present invention relates to use of a method as outlined above for the purification of monoclonal antibodies, in particular for the separation of monomers from dimers and/or multimers.

For process operation, the following parameters need to be determined:
 The duration of the interconnected phases (IC1$a$, IC2$a$ and B1).
 The flow rates in the phases (IC1$a$, IC2$a$ and B1)
 the cleaning and re-equilibration protocol.

All parameters can either be determined a priori or partially a priori. In the latter case online feedback control is required. By means of detectors that are located at the outlet of each adsorber section, online feedback control can be performed.

In case of a priori determination of all operating parameters, the durations of the phases IC1$a$, IC2$a$ can be determined based on breakthrough curves of product and impurities as shown in Example 1. The wash step duration for the duration of phases IC1$b$ and IC2$b$ can be determined by washing experiments of single adsorber sections. The cleaning and re-equilibration procedure for the batch phases B1 and B2 can also be determined in separate experiments using a single adsorber section.

The online feedback control method is based on measuring a signal at the outlet of each of the adsorber sections in the interconnected phase that is proportional to the product concentration. Initially the outflow of the downstream adsorber section only comprises buffer, corresponding to the holdup volume of the adsorber section. The detector signal corresponds to the "zero" baseline. Thereafter, product that is flowing through forms a stable "product" baseline in the detector at the outlet of the upstream adsorber section and likewise in the detector at the outlet of the second adsorber section. As soon as impurities start to break through from the upstream adsorber section the signal recorded at the detector of that adsorber section rises while the signal of the detector of the downstream adsorber section remains at "product" baseline, i.e. the difference of the signals begins to change. Evaluating the signal difference means that it is not required to have the same absolute value of the "product" baseline for the two detectors. This adds robustness to the process control because calibration among the two detectors is not required.

The difference value can be used to trigger the start of interconnected phases IC1$b$ and IC2$b$, respectively.

In phases IC1$b$ and IC2$b$, the washing causes the signal at the detector of the upstream adsorber section to drop. IC1$b$ and IC2$b$, respectively, is completed as soon as the signal at the upstream adsorber section has approached the "zero" baseline, i.e. as soon as the product has been washed out of the upstream adsorber section.

The duration of the subsequent batch phases, B1 and B2, respectively, is dependent on the duration of the cleaning and re-equilibration steps which have been identified a prior through separate experiments. Also in the batch phase the detectors can be used for control purposes: The signal recorded by the detector that is located behind the adsorber section that is loaded with feed mixture (embodiment C), reaches a baseline plateau which is indicative of the product flowing through. A rise from this baseline is indicative of impurity breakthrough in which case the loading must be stopped to avoid product contamination with impurities that break through.

The feed flow rate in general is operated at its maximum value which is dictated by equipment and adsorber device backpressure constraints.

The control approaches for the individual interconnected and batch steps taken together form an overall control concept for the process.

Thus, summarizing, for process contol, a (UV) signal can be recorded at the outlet of each adsorber section and the changes in the (UV) signal over time during the phases IC1$a$, IC1$b$ and/or B1 are used to determine the duration of the phases as defined by $t_{IC_a}$, $t_{IC_b}$ and $t_B$. The determined phase durations are also valid for the phases IC2$a$, IC2$b$ and/or B2, respectively.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

The Process in General

Figure 1:
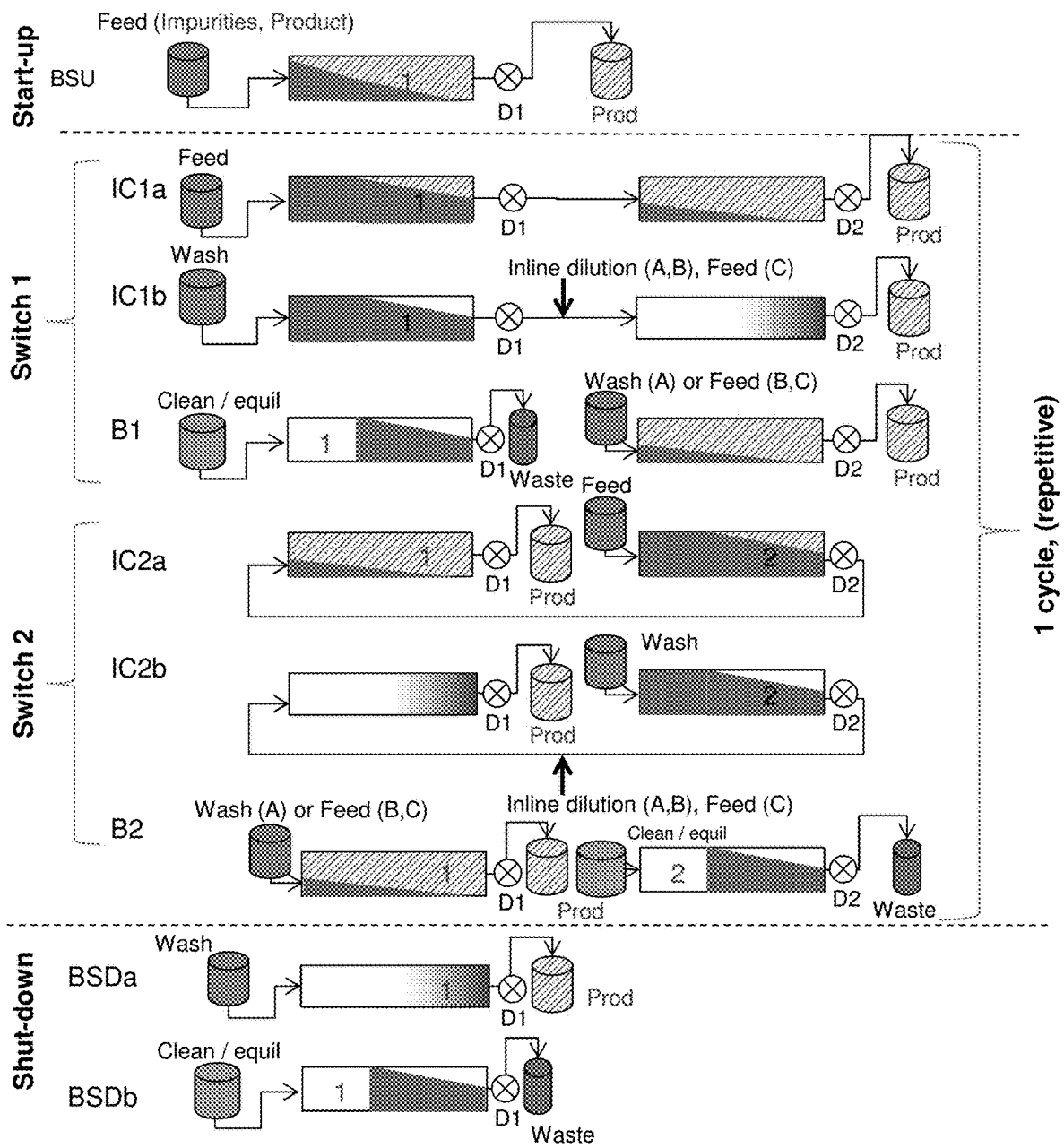
FIG. 1 shows a schematic of the presented flow-through process with two adsorber sections.

As indicated, FIG. 1 shows a schematic of the presented flow-through process with two adsorber sections. The schematic includes the batch startup step (BSU) that is carried out initially only. One process cycle comprises the phases IC1a, IC1b, B1 ("switch 1") and IC2a, IC2b, B2 ("switch 2"). The tasks carried out in switch 2 are identical to the tasks of switch 1, just with the adsorber sections operated in opposite order (or with interchanged positions), i.e. with tasks of adsorber section 1 and adsorber section 2 being exchanged. In interconnected steps IC1a and IC2a, feed mixture is applied to one adsorber section and the flow-through is directed into a second adsorber section. The outflow of the second downstream adsorber section is collected as product. In interconnected steps IC1b and IC2b, the upstream adsorber section is washed with buffer and the stream exiting the first adsorber is either diluted inline with buffer (embodiments A and B) or inline supplied with feed (embodiment C).

In steps B1 and B2 the adsorber sections are disconnected and the formerly upstream adsorber section is cleaned and re-equilibrated while the formerly downstream adsorber section is washed with buffer (embodiment A) or continued to be loaded with feed (embodiments B and C).

One process cycle can be repeated multiple times. The cyclic phase is followed by a shut-down phase where the formerly downstream adsorber section is washed and cleaned (steps BSDa and BSDb).

The process is controlled using detectors are located at each section outlet (D1, D2).

Figure 2:
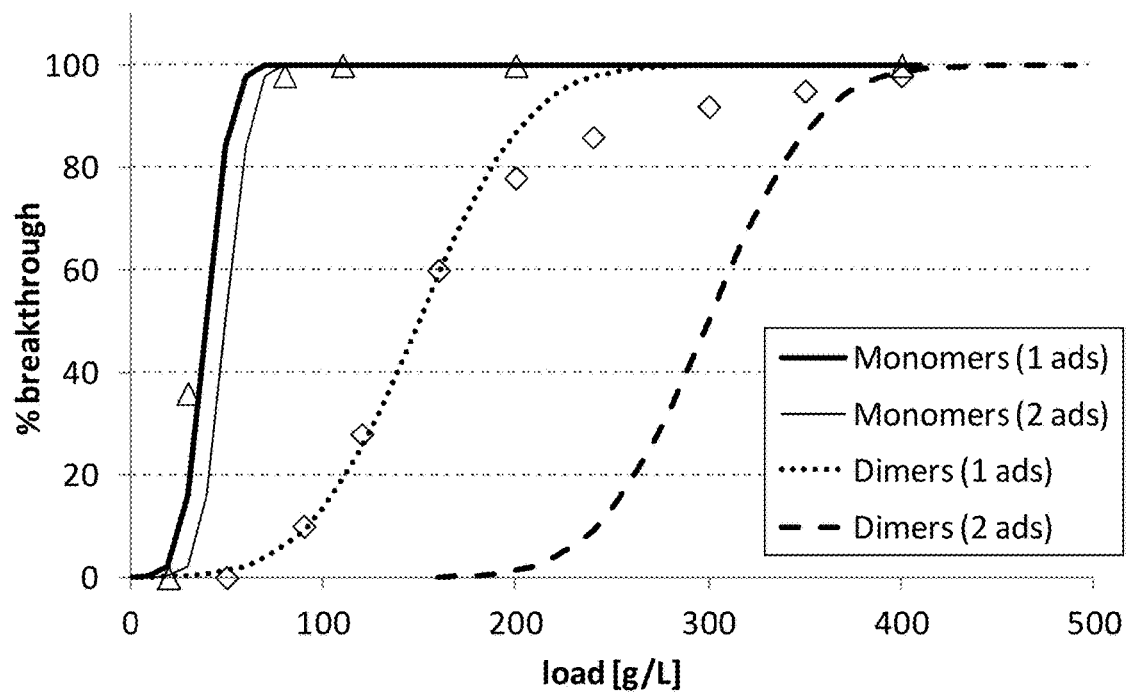
FIG. 2 shows the results of a size exclusion chromatography (SEC) analysis of fractions of a flow-through chromatography run with a monoclonal antibody (mAb) on a single commercially available membrane adsorber (Pall Mustang® S)

Monoclonal Antibody Purification, Load Amount and Capacity Utilization:

A feed containing antibody monomers and dimers is loaded onto Pall Mustang S adsorbers. FIG. 2 shows the results of a size exclusion chromatography (SEC) analysis of fractions of a flow-through chromatography run with a monoclonal antibody (mAb) on a single commercially available membrane adsorber (Pall Mustang® S). On the x-axis, the total loading of mAb on the adsorber is shown in g/L and on the y-axis, the breakthrough value is shown, i.e. the concentration of mAb monomer at the adsorber outlet divided by the concentration of mAb monomer at the adsorber inlet during loading with feed (triangles). Likewise, the breakthrough value of the dimers is shown as a function of the mAb load (diamonds).

To simplify evaluation, the experimental data-points were fitted using mathematical functions (thick full line and dotted lines, respectively).

Simulated breakthrough curves are shown for mAb and dimers loaded onto two membrane adsorbers connected in series (thin full line and thick dashed line, respectively).

FIG. 2 shows the early breakthrough of the product (mAb). Initially the mAb concentration is at zero because the adsorber is equilibrated and devoid of mAb. The breakthrough of mAb occurs slightly later, when two adsorbers are loaded in series because of the increased holdup volume. The dimers, which are considered to be the impurities, are adsorbed stronger than the mAb and elute later, displaying a much shallower breakthrough curve, which indicates that the dimers are adsorbed much stronger (dotted line).

When loading two adsorbers in series such as in the presented process in phases IC1a and IC2a the breakthrough of dimers occurs even later.

In the example a concentration of 20.0 g/L mAb and 1.0 g/L dimer are present in the feed stream. A typical product specification is 99.5% purity i.e. ≤0.5% dimer content.

Figure 3:
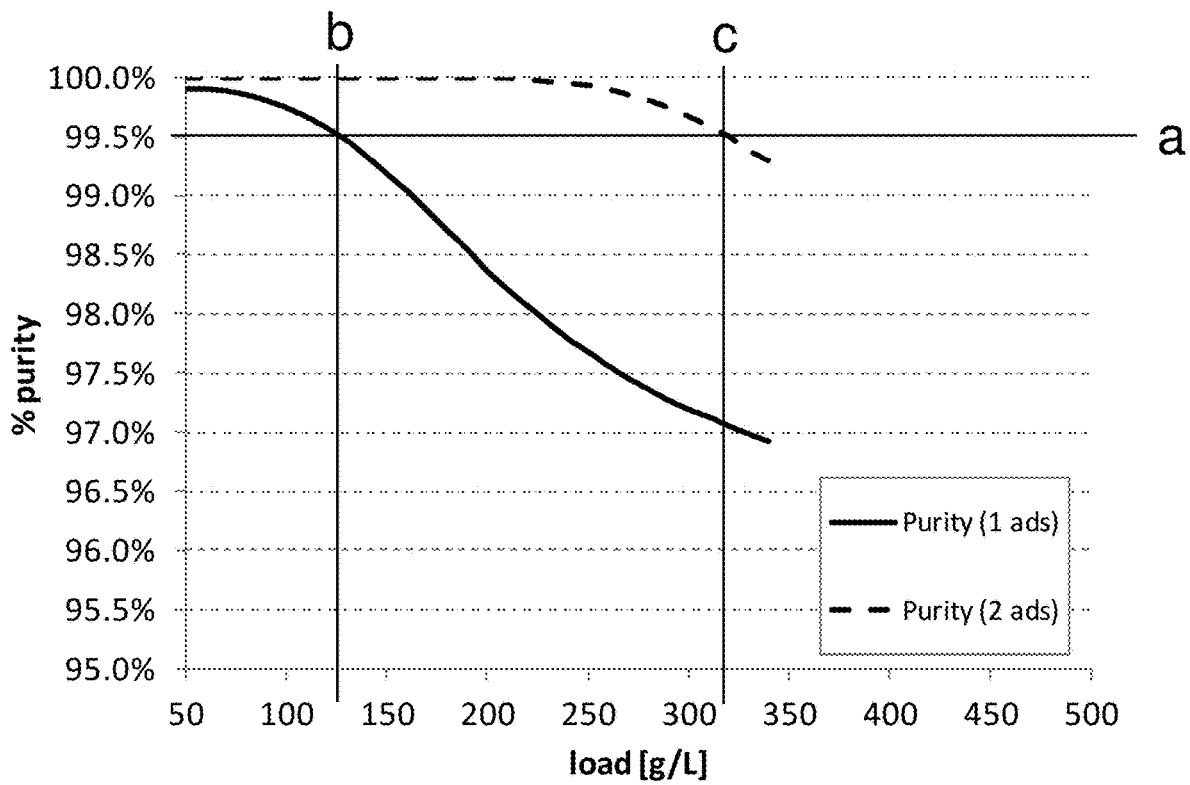
FIG. 3 shows the purity of the mAb pool collected when a single adsorber is loaded (solid line) and when two adsorbers are loaded in series (dashed line)

FIG. 3 shows the purity of the mAb pool collected when a single adsorber is loaded (solid line) and when two adsorbers are loaded in series (dashed line).

The purity is shown as a function of the mAb load. The purity specification of 99.5% (equals 0.5% dimers) is indicated by line "a". The vertical lines "b" and "c" indicate the load that corresponds to the product pool purity matching the purity specification for the single adsorber and for two adsorbers connected in series, respectively.

FIG. 3 shows that overproportionally more mAb can be loaded, maintaining the purity specification, when loading two adsorbers in series (320 g/L) than in the single adsorber case (130 g/L). Loading a single adsorber beyond 130 g/L would lead to a product pool that is out of specification. Likewise, in a setup where two adsorbers are connected in series, loading the upstream adsorber beyond 320 g/L would lead to a product pool that is out of specification.

The maximum available binding capacity of the adsorbers for dimers is given by the area confined by the breakthrough curve, the 100% breakthrough line and the 0 g/L load border. When loading a single adsorber up to the load of 130 g/L, around 80% of the dimer capacity of the membrane adsorber is utilized for dimer adsorption. When loading two adsorbers in series, the capacity utilization of the upstream membrane adsorber by dimers is 100%.

Monoclonal Antibody Purification, Washing and Inline Dilution

After the loading has been completed to the levels commanded by the specifications, the mAb present in the holdup volume of the adsorbers and the adsorbed mAb have to be washed out and recovered in order to avoid yield losses. In traditional processing utmost care has to be taken when selecting and applying washing buffers in order to avoid release of bound impurities and contamination of the product pool. In cases of mAbs and dimers having very similar adsorptive properties, it may not be possible to recover the remaining mAb and to fulfil the specifications at the same time. In that case, the remaining mAb has to be discarded partially or completely. Therefore, flow-through processes for the purification of product from impurities with similar adsorptive properties frequently are reported to have rather low product recoveries of 80-90%.

Assuming a mAb with an isoelectric point (pI) of 8.0 is to be separated from impurities with an isoelectric point of pI=8.5. For the sake of simplicity it is assumed that adsorptive behavior is solely dependent on the charge according to the isoelectric point. In order to separate the mAb and the impurities on a cation exchange adsorber, the pH of the feed material needs to be adjusted to a value in between pH 8.0 and pH 8.5, to ensure that the mAb is breaks through and can be recovered and that the impurities remain adsorbed.

In reality it may be difficult to reproducibly adjust the feed to the same pH value. If the pH is adjusted to too high a value close to pH 8.5, there is risk of impurity release. If the pH is adjusted to a value too close to pH 8.0 there is the risk of product adsorption and subsequent loss in the cleaning phase.

The same holds true for the washing step that follows the loading phase. In practice fulfilling the purity specification is critical so one would try to operate at a pH close to 8.0, which would lead to a fraction of the mAb remaining in the adsorber, which is then lost in the subsequent cleaning step.

The presented process efficiently addresses this drawback in the interconnected washing step IC1$b$ and IC2$b$, respectively, by enabling two different conditions in the two interconnected membrane adsorbers due to inline dilution.

Translated to the above case this means that the mAb can be washed out of the upstream adsorber at a pH of 8.5 which favors mAb desorption and may also release impurities. However using inline dilution, the pH of the stream exiting the upstream adsorber can be adjusted before entering the downstream adsorber. In this case the pH can be adjusted to 8.0 or even below to ensure that no impurities exit the downstream adsorber. By using this approach, all mAb can be washed out of the upstream adsorber. The upstream adsorber can then be cleaned and re-equilibrated in the subsequent batch steps B1 and B2, respectively, without mAb losses.

Regeneration

After having loaded the amounts indicated in example 1 on the adsorbers (130 g/L and 320 g/L onto one and two adsorbers in series, respectively), the adsorbers have to be regenerated, i.e. the dimers have to be removed.

In the proposed process the adsorber sections are disconnected and the formerly upstream adsorber section is cleaned and re-equilibrated using the following protocol:

20 membrane volumes (MV) for cleaning, 20 MV for a first equilibration and 20 MV for a second re-equilibration. The flow rate is 10 MV/min, leading to a total time required for cleaning and re-equilibration of 7 min.

In comparison, a process with two adsorber sections being cleaned in series would require 14 min for cleaning since the double adsorber volume would need to be treated using the same flow rate.

Process Design of Novel Process and Process Comparison, High Feed Titer

The presented process can in particular be used in the polishing of biomolecules, i.e. in intermediate chromatography steps, following initial different purification steps. In monoclonal antibody purification, such polishing steps are usually operated with mAb concentrations in the feed material (feed titers) of 10-20 g/L and are used for removal of product related impurities such as aggregates and for DNA, Host Cell Protein and virus removal.

The process parameters, i.e. the duration of the individual steps IC1, IC2, B are determined based on a number of input parameters that are listed in the table below in the shaded fields.

They include the feed mAb monomer concentration (i.e. the product concentration) and the feed dimer concentration (i.e. the impurity concentration) in [g/L], the volumes of the adsorber devices, the possible load corresponding to the product pool being in specification (see example 1) for a single adsorber section and two adsorber sections loaded in series, the protocols for washing, cleaning and re-equilibration in terms of adsorber volumes [AV], the flow rates in terms of adsorber volumes per minute [AV/min] and the yield that corresponds to the product being in specification. All input parameters can be determined a priori in separate experiments.

For the presented process, the maximum possible flow rates should be chosen. The flow rate is limited by adsorber device specification and equipment flow rates and back pressure limits.

In this example a first setup using a single adsorber section is compared to a second setup using two adsorber sections connected in series, representing the state of the art, and to a third setup representing process embodiment A and to a fourth setup representing process embodiment B.

According to example 1, the load of the single adsorber section process was 130 g/L and the load of the process with two adsorber sections interconnected was 320 g/L. Embodiment A has the same load as the latter setup since it only features interconnected loading phases (IC1$a$, IC2$a$) while embodiment B features two types of loading phases (IC1$a$, IC2$a$), and (B1, B2) and embodiment C features three types of loading phases (IC1$a$, IC2$a$), (IC1$b$, IC2$b$) and (B1, B2).

Therefore in embodiments B and C, the load is split among these two and three types of phases, respectively.

The load flow rate in interconnected loading phases in terms of [AV/min] was selected half of the flow rate of the single adsorber sections (5 AV/min vs. 10 AV/min) in order to use the same volumetic flow rate in the calculations in [mL/min] for correct process comparison.

The remaining process parameters, i.e. the load volumes and the times of the individual interconnected and batch phases can be calculated from the input parameters.

Finally, productivity in terms of gram of mAb produced per adsorber volume and per processing time can be calculated and compared. Likewise buffer consumption in terms of Liters of buffer consumed per gram of antibody purified can be compared among the processes. The example shows the advantage of the presented process embodiments A and B in terms of productivity and buffer consumption over the state of the art processes for a high product concentration in the feed mixture while fulfilling the purity specification of 99.5%. Embodiment C is not favorable in this high titer scenario due to the low applicable feed flow rate.

TABLE 1

Process input and performance parameters for state of the art processes and embodiments A-C for a high feed titer scenario

|  |  | 1 adsorber state of art | 2 adsorbers state of art | 2 adsorbers new process embodiment A | 2 adsorbers new process embodiment B | 2 adsorbers new process embodiment C |
|---|---|---|---|---|---|---|
| Feed: Monomer concentration | [g/L] | 20 | 20 | 20 | 20 | 20 |
| Feed: Dimer concentration | [g/L] | 1 | 1 | 1 | 1 | 1 |
| Load IC1a, IC2a | [g/L] | 0 | 320 | 320 | 255 | 220 |
| Load IC1b, IC2b | [g/L] | 0 | 0 | 0 | 0 | 50 |
| Load B1, B2 | [g/L] | 130 | 0 | 0 | 65 | 50 |
| Bed volume IC | [mL] | 260 | 520 | 520 | 520 | 520 |
| Bed volume B | [mL] | 260 | 520 | 260 | 260 | 260 |
| Wash volume IC | [AV] | 0 | 10 | 10 | 10 | 10 |
| Wash volume B | [AV] | 10 | 0 | 10 | 0 | 0 |
| CIP | [AV] | 20 | 20 | 20 | 20 | 20 |
| Re-equil 1 | [AV] | 20 | 20 | 20 | 20 | 20 |
| Re-equil 2 | [AV] | 30 | 30 | 30 | 30 | 30 |
| Load Flow rate IC1a, IC2a | [AV/min] | 10 | 5 | 5 | 5 | 0.4 |
| Wash flow rate IC1b, IC2b | [AV/min] | 10 | 5 | 3 | 3 | 1.4 |
| Inline Dil Flow rate | [AV/min] | 0 | 0 | 2 | 2 | 0 |
| Inline Feed Flow rate | [AV/min] | 0 | 0 | 0 | 0 | 0.4 |
| Load Flow rate B | [AV/min] | 10 | 0 | 0.0 | 0.5 | 0.4 |
| Cleaning flow rate | [AV/min] | 10 | 5 | 10 | 10 | 10 |
| yield | [%] | 80% | 80% | 95% | 95% | 95% |
| Load volume IC | [AV] | 0 | 16 | 16 | 12.75 | 11 |
| Load volume B | [AV] | 6.5 | 0 | 0 | 3.25 | 2.5 |
| time for loading IC1 | [min] | 0 | 3.2 | 3.2 | 2.55 | 30.8 |
| time for washing IC2 | [min] | 1 | 2 | 3.33 | 3.33 | 7 |
| time for loading B | [min] | 0.65 | 0 | 0 | 0 | 0 |
| time for cleaning B | [min] | 7 | 14 | 7 | 7 | 7 |
| cycle time | [min] | 8.65 | 19.2 | 27.1 | 25.8 | 89.6 |
| productivity | [g/L/h] | 721 | 800 | 1348 | 1416 | 407 |
| buffer demand | [L/g] | 0.77 | 0.31 | 0.30 | 0.26 | 0.31 |

Process Design of Novel Process and Process Comparison, Low Feed Titer

The proposed process can be used also in the capture of biomolecules where mAb concentrations in the feed material (feed titers) are about one order of magnitude lower than in the polishing steps.

Table 2 shows the results of a study using a feed with a product concentration of 1.5 g/L. Because the ratio of mAb to impurities was the same as in the previous example, the same load volumes are applicable. The investigation was carried out in analogy to the previous example and the results are provided in table 2. The example shows the advantage of the presented process embodiments A, B and C in terms of productivity over the state of the art process using two adsorber sections. Embodiments B and C are also superior in terms of productivity over the state of the art process that uses a single adsorber section while embodiment A is inferior. However all embodiments are advantageous over the state of the art process that uses a single adsorber section in terms of buffer consumption. The process embodiment C is the only process utilizing a constant feed flow rate, in all other processes the feed flow rate is discontinuous. This example shows that embodiment C is very competitive in a low feed titer scenario.

TABLE 2

Process input and performance parameters for state of the art processes and embodiments A-C for a high feed titer scenario

|  |  | 1 adsorber state of art | 2 adsorbers state of art | 2 adsorbers new process embodiment A | 2 adsorbers new process embodiment B | 2 adsorbers new process embodiment C |
|---|---|---|---|---|---|---|
| Feed: Monomer concentration | [g/L] | 1.5 | 1.5 | 1.5 | 1.5 | 1.5 |
| Feed: Dimer concentration | [g/L] | 0.075 | 0.075 | 0.075 | 0.075 | 0.075 |
| Load IC1a, IC2a | [g/L] | 0 | 320 | 320 | 255 | 220 |
| Load IC1b, IC2b | [g/L] | 0 | 0 | 0 | 0 | 50 |
| Load B1, B2 | [g/L] | 130 | 0 | 0 | 65 | 50 |
| Bed volume IC | [mL] | 260 | 520 | 520 | 520 | 520 |
| Bed volume B | [mL] | 260 | 520 | 260 | 260 | 260 |

TABLE 2-continued

Process input and performance parameters for state of the art processes and embodiments A-C for a high feed titer scenario

|  |  | 1 adsorber state of art | 2 adsorbers state of art | 2 adsorbers new process embodiment A | 2 adsorbers new process embodiment B | 2 adsorbers new process embodiment C |
|---|---|---|---|---|---|---|
| Wash volume IC | [AV] | 0 | 10 | 10 | 10 | 10 |
| Wash volume B | [AV] | 10 | 0 | 10 | 0 | 0 |
| CIP | [AV] | 20 | 20 | 20 | 20 | 20 |
| Re-equil 1 | [AV] | 20 | 20 | 20 | 20 | 20 |
| Re-equil 2 | [AV] | 30 | 30 | 30 | 30 | 30 |
| Load Flow rate IC1a, IC2a | [AV/min] | 10 | 5 | 5 | 5 | 4.8 |
| Wash flow rate IC1b, IC2b | [AV/min] | 10 | 5 | 3 | 3 | 1.4 |
| Inline Dil Flow rate | [AV/min] | 0 | 0 | 2 | 2 | 0 |
| Inline Feed Flow rate | [AV/min] | 0 | 0 | 0 | 0 | 4.8 |
| Load Flow rate B | [AV/min] | 10 | 0 | 0.0 | 6.2 | 4.8 |
| Cleaning flow rate | [AV/min] | 10 | 5 | 10 | 10 | 10 |
| yield | [%] | 80% | 80% | 95% | 95% | 95% |
| Load volume IC | [AV] | 0.0 | 213.3 | 213.3 | 170.0 | 146.7 |
| Load volume B | [AV] | 86.7 | 0.0 | 0.0 | 43.3 | 33.3 |
| time for loading IC1 | [min] | 0.0 | 42.7 | 42.7 | 34.0 | 30.8 |
| time for washing IC2 | [min] | 1.0 | 2.0 | 3.3 | 3.3 | 7.0 |
| time for loading B | [min] | 8.7 | 0.0 | 0.0 | 0.0 | 0.0 |
| time for cleaning B | [min] | 7.0 | 14.0 | 7.0 | 7.0 | 7.0 |
| cycle time | [min] | 16.7 | 58.7 | 106.0 | 88.7 | 89.6 |
| productivity | [g/L/h] | 374 | 262 | 344 | 411 | 407 |
| buffer demand | [L/g] | 0.77 | 0.31 | 0.30 | 0.26 | 0.31 |

Operation of the Process, Low Feed Titer

Three runs of the novel process were operated using two membrane adsorbers to remove aggregate impurities from a fusion protein starting material (feed), containing both monomers (92.7%) and aggregates (7.3%). The total protein concentration of the starting material was 1.4 g/L. The pH of the fusion protein was 6.5 and the conductivity was 15.1 mS/cm. The membrane adsorbers used were two Nano S adsorbers (3 mL), Sartorius, Germany. The process was operated using Contichrom CUBE Combined equipment from ChromaCon, Switzerland. The following buffers were used: Buffer A: 25 mM Phosphate pH 6.0; buffer B: 25 mM Phosphate, 500 mM NaCl, pH 6.0; buffer C: 1M NaOH Protein concentration and aggregate content were determined using size exclusion HPLC on a Tosoh TSKgel G3000swxl 4.6×250 mm column using a 0.1 M NaSO4, 25 mM Phosphate buffer at pH 7.0 and a flow rate of 1.0 mL/min, using Agilent 1100 HPLC equipment.

Figure 4:
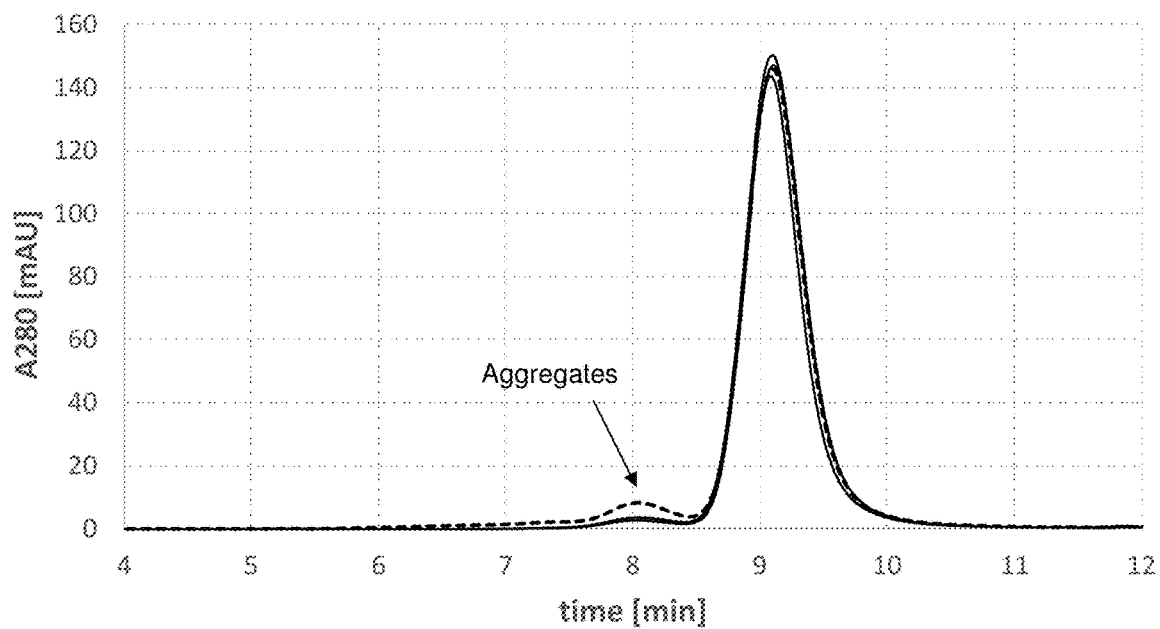
FIG. 4 shows the results of a size exclusion chromatography (SEC) analysis of the starting material (dashed line) and of the product obtained using the novel process (full lines). Aggregates are indicated by the arrow.

A chromatogram of the feed material obtained by analytical size-exclusion chromatography is shown in FIG. 4 (dashed line). The Figure also shows the chromatograms of the product obtained with the novel process (solid lines). The aggregate content of the product was 2.1-2.6%. The parameters of the three runs of the novel process are summarized in Table 3. The runs differed only in the duration of phase IC1a/IC2a, which was 4.0 min in a first case, 5.5 min in a second case and 7.0 min in a third case.

TABLE 3

Operating parameters of three runs of the novel process

| Phase | Parameter | flow rate [mL/min] | duration [min] | Buffer |
|---|---|---|---|---|
| IC1a/IC2a | Feed flow | 12 | 4/5.5/7 | Feed |
| IC1b/IC2b | Wash flow | 6 | 2.5 | washing buffer 50% A, 50% B. |

TABLE 3-continued

Operating parameters of three runs of the novel process

| Phase | Parameter | flow rate [mL/min] | duration [min] | Buffer |
|---|---|---|---|---|
| IC1b/IC2b | inline dilution flow | 6 | 2.5 | buffer A |
| B1/B2 | Wash flow | 12 | 2.5 | buffer A |
| B1/B2 | Elution | 12 | 2.5 | buffer B |
| B1/B2 | cleaning | 12 | 2.5 | 1M NaOH |
| B1/B2 | equil 1 | 12 | 2.5 | buffer B |
| B1/B2 | equil 2 | 12 | 3 | buffer A |

During the run, the flow-through containing the product of interest was collected and analyzed using size exclusion chromatography to determine the protein concentration and aggregate content and to calculate product yield and purity. As reference, breakthrough curve were run at 12 mL/min using the same starting material, representing a traditional flow-through process.

Figure 5:
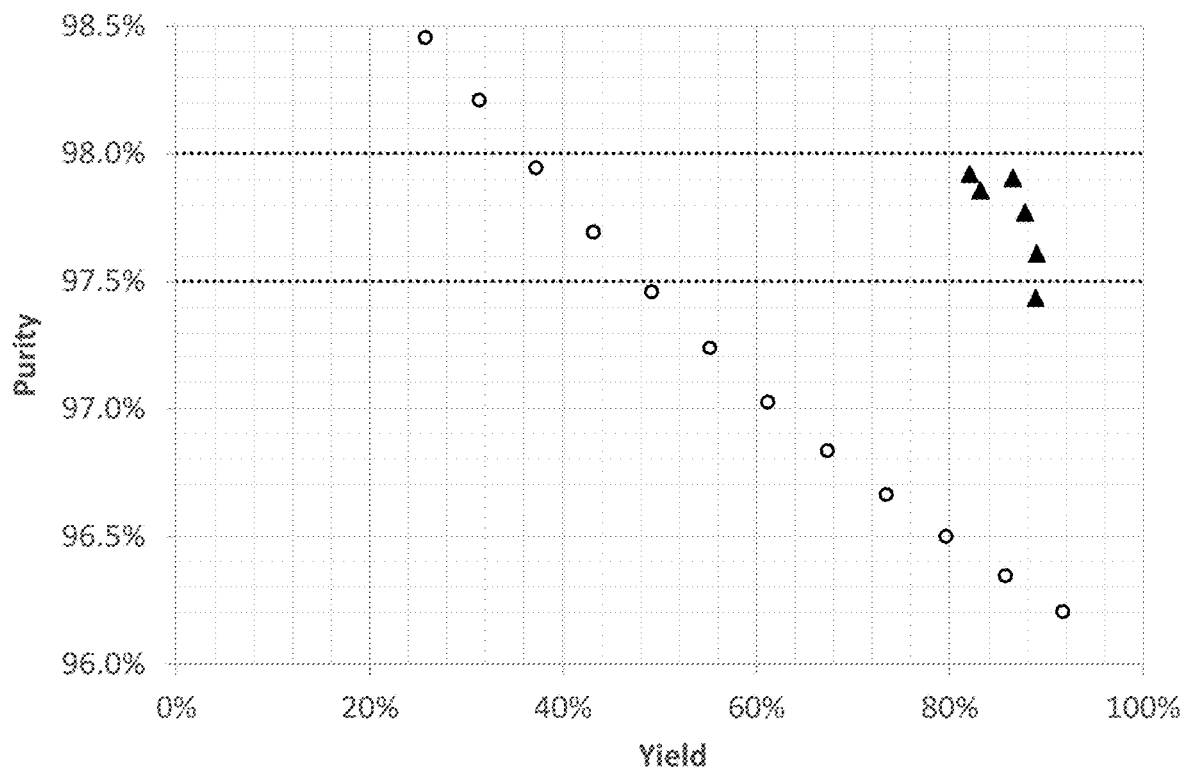
FIG. 5 Purity vs. yield chart for the novel process (black triangles) and the batch reference process (empty circles)

In FIG. 5 the results of the breakthrough analysis and the results obtained from the novel process are shown as purity-yield chart. For the novel process, two cycles in steady state are shown for each of the three runs, resulting in 6 data points in total (filled triangles). It can be seen that in the purity interval of 97.5-98.0%, the yield of the product obtained with the novel process is 80-90% while the yield of the traditional flow-through process is in the range of 35-50% (circles). Thus, significant advantages are obtained using the novel process with respect to purity/yield.

Figure 6:
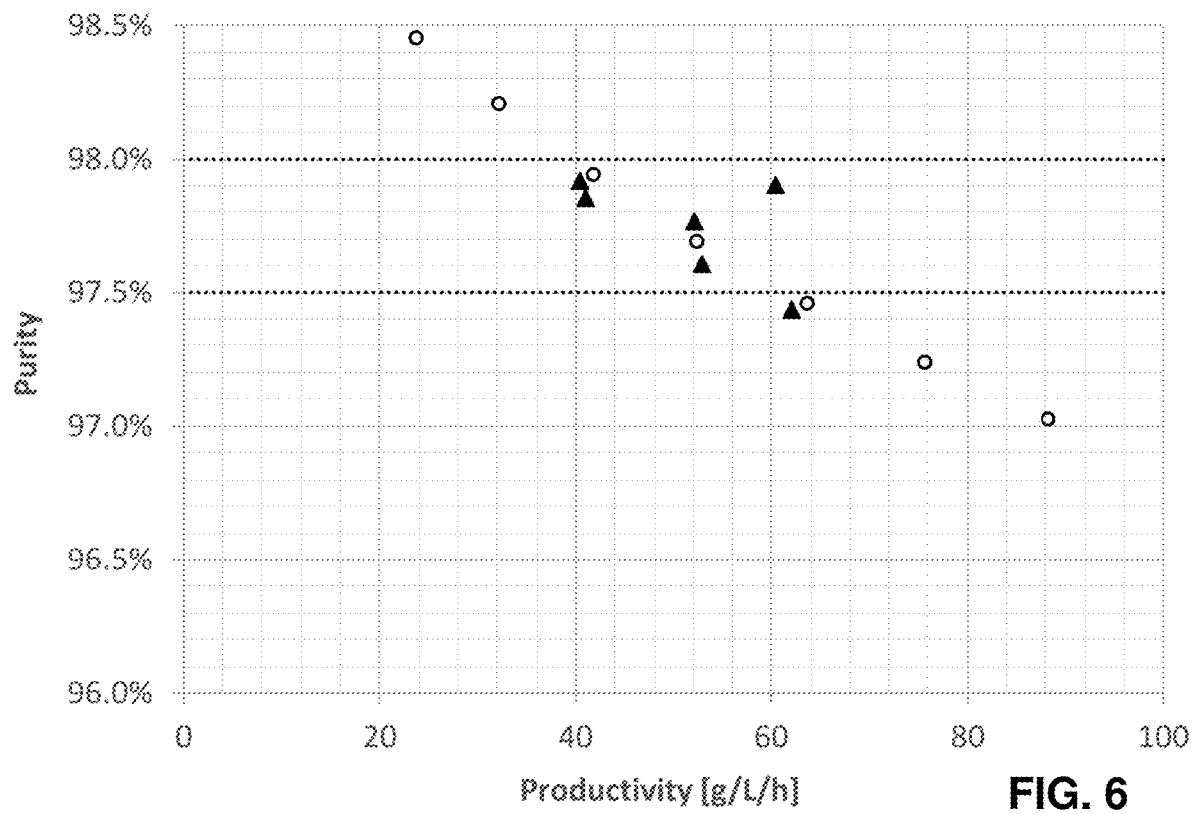
FIG. 6 Purity vs. Productivity chart for the novel process (black triangles) and the batch reference process (empty circles)

An evaluation of the purity as a function of the productivity shows that the new process (filled triangles) reaches similar values as the traditional process (circles), which means that the output and product quality is comparable (FIG. 6). However with the traditional flow-through process almost twice as much starting material is required to achieve the same output in terms of mass of product per time unit and adsorber volume due to the lower yield.

Figure 7:
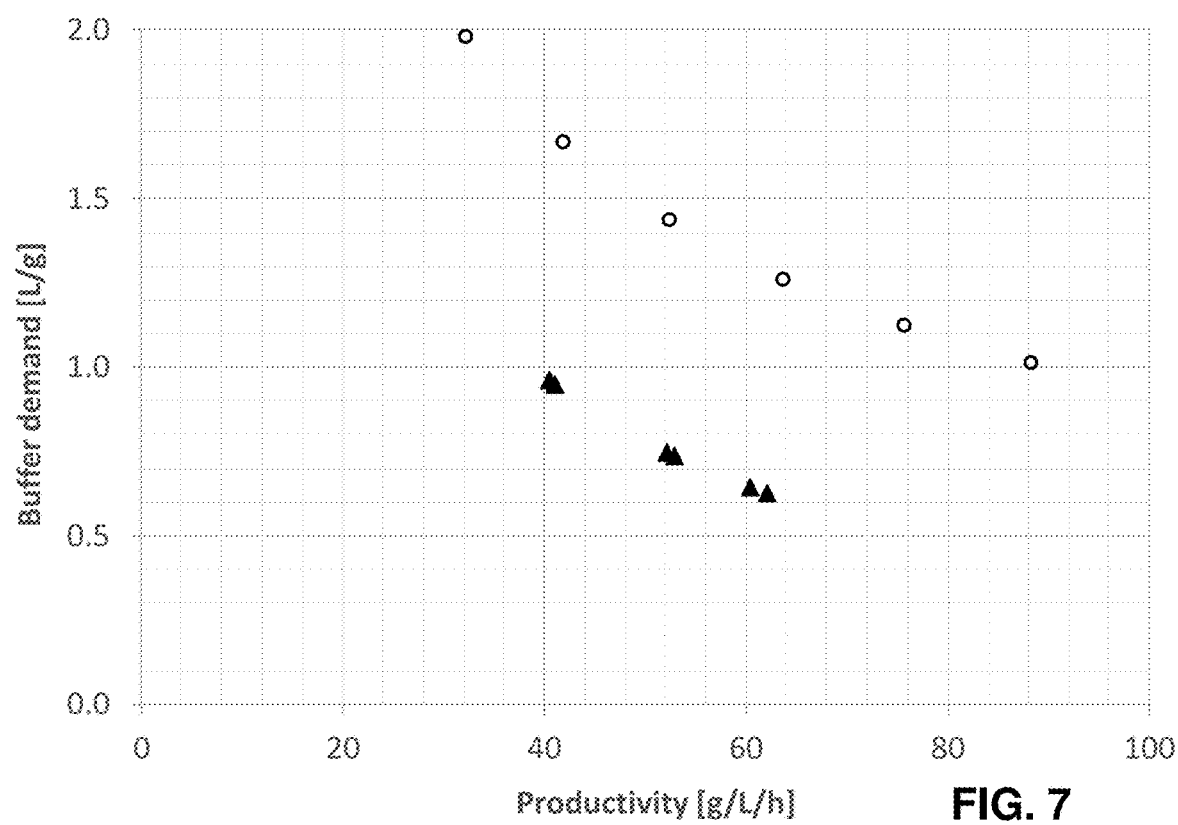
FIG. 7 Buffer demand vs. productivity chart for the novel process (black triangles) and the batch reference process (empty circles).

The buffer consumption as a function of the productivity is shown in FIG. 7. Due to its high yield, the novel process demonstrated in the example (filled triangles) also has an almost 50% lower specific buffer consumption than the traditional flow-through process (circles).

Summarizing, the high yield in combination with the lower buffer consumption reduces losses of expensive protein during the purification and significantly reduces buffer costs.

LIST OF REFERENCE SIGNS

| | |
|---|---|
| IC1a | first interconnected state or phase of the flow-through process |
| IC1b | second interconnected state or phase of the flow-through process |
| IC2a | third interconnected state or phase of the flow-through process |
| IC2b | fourth interconnected state or phase of the flow-through process |
| B1 | first disconnected state or phase (batch state) of the flow-through process |
| B2 | second disconnected state or phase (batch state) of the flow-through process |
| $t_{ICa}$ | first interconnected timespan, duration of phases IC1a and IC2a, respectively |
| $t_{ICb}$ | second interconnected timespan, duration of phases IC1b and IC2b, respectively |
| $t_B$ | batch timespan, duration of the disconnected phases B1 and B2, respectively |
| BSU | batch Startup Phase of the flow-through process |
| $t_{BSU}$ | duration of the Batch Startup Phase |
| BSD | Batch Shutdown Phase of the flow-through process |
| $t_{BSDa}$ | duration of the first part of the Batch Shutdown Phase |
| $t_{BSDb}$ | duration of the second part of the Batch Shutdown Phase |

The invention claimed is:

1. A cyclic chromatographic purification method for the isolation of a product from a feed mixture comprising the product and at least one further component representing impurities, which impurities bind stronger to a chromatographic stationary phase than the product,
   the method using at least two chromatographic non-affinity adsorbers as a chromatographic stationary phase, said at least two chromatographic non-affinity adsorbers being grouped into only one first adsorber section and one second adsorber section, there being no adsorber sections used other than said first and second adsorber sections,
   wherein if either of said only two adsorber sections comprises more than one chromatographic adsorber, said more than one chromatographic adsorber in an adsorber section are permanently connected in series,
   wherein the first adsorber section has a first adsorber section inlet and a first adsorber section outlet, and the second adsorber section has a second adsorber section inlet and a second adsorber section outlet,
   the method comprising the following steps in order:
   a. a first interconnected step,
      wherein the first adsorber section outlet is connected to the second adsorber section inlet during a first interconnected timespan,
      wherein the first adsorber section is loaded via the first adsorber section inlet with the feed mixture, and
      wherein the product is collected from the second adsorber section outlet;
   b. a second interconnected step conducted directly after said first interconnected step without disconnection,
      wherein the first adsorber section outlet is connected to the second adsorber section inlet during a second interconnected timespan,
      wherein the first adsorber section is loaded via the first adsorber section inlet with a first washing buffer to transfer the product unbound in the first absorber section into the second adsorber section,
      wherein a stream exiting the first adsorber section outlet is either:
         diluted inline before entering the second adsorber section inlet, or
         supplemented with the feed mixture, and
      wherein the product is collected from the second adsorber section outlet;
   c. a first batch step,
      wherein during a batch timespan said first and second adsorber sections are disconnected,
      wherein the first adsorber section is cleaned and regenerated to remove the impurities and the first adsorber section outlet is directed to waste,
      wherein the second adsorber section inlet is either:
         loaded with a second washing buffer, or
         loaded with the feed mixture, and
         wherein the product is collected from the second adsorber section outlet;
   d. a third interconnected step,
      wherein the first adsorber section performs tasks of the second adsorber section in the first interconnected step, and the second adsorber section performs tasks of the first adsorber section in the first interconnected step;
   e. a fourth interconnected step conducted directly after said third interconnected step without disconnection,
      wherein the first adsorber section performs tasks of the second adsorber section in the second interconnected step, and the second adsorber section performs tasks of the first adsorber section in the second interconnected step; and
   f. a second batch step,
      wherein the first adsorber section performs tasks of the second adsorber section in the first batch step, and the second adsorber section performs tasks of the first adsorber section in the first batch step.

2. The method according to claim 1 wherein each adsorber section consists of only one adsorber such the total number of adsorbers in the process is two.

3. The method according to claim 1, wherein before for a first time carrying out the first interconnected step a start-up step is carried out, in which during a start-up batch timespan said adsorber sections are disconnected and an equilibrated adsorber section to be taking the place of the first adsorber section in the subsequent first interconnected step is loaded with the feed mixture via the first adsorber section inlet and the product is collected from the first adsorber section outlet, while the second adsorber section is either being equilibrated or already equilibrated and inactive.

4. The method according to claim 1,
   wherein after termination of the desired cycles of steps a.-f. the method is followed by a shut-down sequence,
   wherein during a shut-down batch timespan said first and second adsorber sections are disconnected and one adsorber section of the first and second adsorber sections, which had been subjected to washing in a preceding second batch step, is washed such that the product is collected from the one adsorber section at its outlet; and wherein during a regeneration timespan said adsorber section is regenerated.

5. The method according to claim 1,
wherein the chromatographic stationary phase in the adsorbers is in the form of at least one of particles, beads, membranes, monoliths or fibers, and
wherein the adsorbers are single-use or multi-use devices.

6. The method according to claim 1 wherein the chromatographic adsorption is based on hydrophobic interaction, multi-modal interaction or ion exchange.

7. The method according to claim 1,
wherein a detector is located at the outlet of each adsorber section and
wherein changes in a detected signal over time during the first and second interconnected steps are used to determine the first and second interconnected timespans, respectively.

8. The method according to claim 7, wherein the detector is selected from the group consisting of: a UV detector, a visible light detector, an IR detector, a fluorescence detector, a light scattering detector, a refractive index detector, a pH detector, a conductivity detector, an at-line HPLC detector, and a mass spectrometry detector.

9. The method according to claim 1,
wherein the product is one selected from the group consisting of: a chemical reaction product, a biochemical reaction product, and a biological product, and
wherein the reaction products include natural products, metals, antibodies, antibody fragments, fusion proteins, recombinant glycoproteins, plasma proteins, or derivatives, combinations and mixtures thereof.

10. The method according to claim 1, wherein the product is an antibody monomer and the impurities include at least one antibody dimer and/or multimer.

11. The method according to claim 1,
wherein in the second interconnected step a stream exiting the first adsorber section outlet is diluted inline before entering the second adsorber section inlet, and
wherein in the first batch step the second adsorber section inlet is loaded with a second washing buffer.

12. The method according to claim 1,
wherein in the second interconnected step a stream exiting the first adsorber section outlet is diluted inline before entering the second adsorber section inlet, and
wherein in the first batch step the second adsorber section inlet is loaded with the feed mixture.

13. The method according to claim 1,
wherein in the second interconnected step a stream exiting the first adsorber section outlet is supplemented with the feed mixture before entering the second adsorber section inlet, and
wherein in the first batch step a second adsorber section inlet is loaded with the feed mixture.

14. The method according to claim 1, wherein in the second interconnected step a stream exiting the first adsorber section outlet is diluted inline before entering the second adsorber section inlet with a third washing buffer.

15. The method according to claim 1 for the purification of monoclonal antibodies.

16. The method according to claim 1, wherein the chromatographic stationary phase in the adsorbers is a non-affinity material that withholds the product and the impurities, depending on their chemical nature, in a gradual manner.

17. The method according to claim 1,
wherein in the second interconnected step a stream exiting the first adsorber section outlet is diluted inline before entering the second adsorber section inlet,
wherein in the first batch step the second adsorber section inlet is loaded with a second washing buffer, and
wherein in the fourth interconnected step a stream exiting the second adsorber section outlet is diluted inline before entering the first adsorber section inlet, and
wherein in the first batch step the first adsorber section inlet is loaded with a second washing buffer.

18. The method according to claim 1,
wherein in the second interconnected step a stream exiting the first adsorber section outlet is diluted inline before entering the second adsorber section inlet,
wherein in the first batch step the second adsorber section inlet is loaded with the feed mixture,
wherein in the fourth interconnected step a stream exiting the second adsorber section outlet is diluted inline before entering the first adsorber section inlet, and
wherein in the first batch step the first adsorber section inlet is loaded with the feed mixture.

19. The method according to claim 1,
wherein in the second interconnected step a stream exiting the first adsorber section outlet is supplemented with the feed mixture before entering the second adsorber section inlet,
wherein in the first batch step the second adsorber section inlet is loaded with the feed mixture,
wherein in the fourth interconnected step a stream exiting the second adsorber section outlet is supplemented with the feed mixture before entering the first adsorber section inlet, and
wherein in the first batch step the first adsorber section inlet is loaded with the feed mixture.

20. The method according to claim 1,
wherein in the second interconnected step a stream exiting the first adsorber section outlet is diluted inline before entering the second adsorber section inlet with a third washing buffer, and
wherein in the fourth interconnected step a stream exiting the second adsorber section outlet is diluted inline before entering the first adsorber section inlet with a third washing buffer.

21. The method according to claim 1 for the purification of monoclonal antibodies, for the separation of monomers from dimers and/or multimers.

22. The method according to claim 8, wherein IR detector is selected from the group consisting of: VIS and IR Raman detectors.

23. The method according to claim 1,
wherein the product is one selected from the group consisting of: a plurality of chemical reaction products, a plurality of chemical separation products, a plurality of biochemical reaction products, and a plurality of biological products, and
wherein the reaction products include natural products, metals, antibodies, antibody fragments, fusion proteins, recombinant glycoproteins, plasma proteins, or derivatives.

* * * * *